(12) United States Patent
Ruddocks et al.

(10) Patent No.: US 10,537,683 B2
(45) Date of Patent: Jan. 21, 2020

(54) SYRINGE FINGER GRIP

(71) Applicant: Abbott Medical Optics Inc., Santa Ana, CA (US)

(72) Inventors: David A. Ruddocks, Mission Viejo, CA (US); Walter A. York, Mission Viejo, CA (US); Brent L. Burchfield, Powell, OH (US); Jeffrey R. Burger, Bexley, OH (US); Joseph M. Lehman, New Albany, OH (US); Neal J. Kelly, Pomona, CA (US); Ken P. Monk, Elk River, MN (US); James R. Rowland, Bolivar, OH (US); Nicole M. Samuelson, San Francisco, CA (US)

(73) Assignee: Johnson & Johnson Surgical Vision, Inc., Santa Ana, CA (US)

( * ) Notice: Subject to any disclaimer, the term of this patent is extended or adjusted under 35 U.S.C. 154(b) by 294 days.

(21) Appl. No.: 15/343,109

(22) Filed: Nov. 3, 2016

(65) Prior Publication Data

US 2018/0117256 A1   May 3, 2018

(51) Int. Cl.
*A61M 5/31* (2006.01)
*A61F 9/00* (2006.01)

(52) U.S. Cl.
CPC .......... *A61M 5/3137* (2013.01); *A61F 9/0017* (2013.01); *A61M 2005/3139* (2013.01)

(58) Field of Classification Search
CPC ........ A61M 5/3137; A61M 2005/3139; A61M 2005/1458
See application file for complete search history.

(56) References Cited

U.S. PATENT DOCUMENTS

| | | |
|---|---|---|
| 3,026,873 A | 3/1962 | Miskel et al. |
| 3,220,412 A | 11/1965 | McConnaughey et al. |
| 4,643,724 A | 2/1987 | Jobe |
| 4,743,234 A | 5/1988 | Leopoldi et al. |
| 5,419,775 A | 5/1995 | Haffner et al. |
| 5,509,903 A | 4/1996 | Grendahl et al. |

(Continued)

FOREIGN PATENT DOCUMENTS

| | | |
|---|---|---|
| AU | 2009261314 A1 | 12/2009 |
| AU | 2011310580 B2 | 12/2014 |

(Continued)

OTHER PUBLICATIONS

International Search Report and Written Opinion for Application No. PCT/US2017/060032, dated Feb. 20, 2018, 13 pages.

*Primary Examiner* — Nilay J Shah
(74) *Attorney, Agent, or Firm* — Johnson & Johnson Surgical Vision, Inc.

(57) ABSTRACT

A finger grip for receiving and retaining a syringe body of an injection syringe. The finger grip is easily pressed directly onto the syringe and employs a centering feature and a pair of one way, flexible latches that allow easy attachment to a syringe body yet ensures retention during normal and abnormal use. If a high horizontal component force is applied during normal or abnormal use, the finger grip will not become disconnected in an uncontrolled fashion from the syringe body, which might cause injury and/or damage to a patient being injected. The flexible latches may prevent detachment of the finger grip from the syringe below separation force of about 25 lbs.

14 Claims, 5 Drawing Sheets

(56) References Cited

U.S. PATENT DOCUMENTS

| | | |
|---|---|---|
| 5,554,133 A | 9/1996 | Haffner et al. |
| 5,607,399 A | 3/1997 | Grimard et al. |
| 5,667,495 A | 9/1997 | Bitdinger et al. |
| 5,700,247 A | 12/1997 | Grimard et al. |
| 5,803,918 A | 9/1998 | Vetter et al. |
| 5,897,532 A | 4/1999 | Spallek et al. |
| 5,925,032 A | 7/1999 | Clements |
| 5,984,901 A | 11/1999 | Sudo et al. |
| 5,997,514 A | 12/1999 | Balestracci |
| D419,671 S | 1/2000 | Jansen |
| D434,850 S | 12/2000 | Balestracci |
| 6,296,625 B1 | 10/2001 | Vetter et al. |
| 6,344,032 B1 | 2/2002 | Perez et al. |
| 6,936,033 B2 | 8/2005 | McIntosh et al. |
| 7,033,343 B2 | 4/2006 | McWethy et al. |
| D581,527 S | 11/2008 | Jansen |
| 7,488,307 B2 | 2/2009 | Rimlinger et al. |
| 7,601,140 B2 | 10/2009 | Rossback et al. |
| 7,691,085 B2 | 4/2010 | Dedig et al. |
| 7,794,435 B2 | 9/2010 | Nemoto |
| 7,846,136 B2 | 12/2010 | Witowski |
| 7,875,007 B2 | 1/2011 | Perot et al. |
| 7,951,120 B2 | 5/2011 | Wolbring et al. |
| 7,954,672 B2 | 6/2011 | Keller |
| 8,016,795 B2 | 9/2011 | Barrelle et al. |
| D649,242 S | 11/2011 | Kosinski et al. |
| 8,075,535 B2 | 12/2011 | Carred et al. |
| D663,023 S | 7/2012 | Strong et al. |
| 8,240,511 B2 | 8/2012 | Greter et al. |
| D710,005 S | 7/2014 | Kawamura |
| 8,920,385 B2 | 12/2014 | Dowds |
| 9,289,555 B2 | 3/2016 | Anelli et al. |
| 9,387,292 B2 | 7/2016 | Dowds |
| 2003/0220615 A1 | 11/2003 | Fabian et al. |
| 2004/0034323 A1 | 2/2004 | Manthey |
| 2005/0192544 A1 | 9/2005 | Wolbring et al. |
| 2006/0161114 A1 | 7/2006 | Perot et al. |
| 2009/0036839 A1 | 2/2009 | Phalen |
| 2010/0016805 A1 | 1/2010 | Painchaud et al. |
| 2011/0087173 A1 | 4/2011 | Sibbitt, Jr. et al. |
| 2011/0190709 A1 | 8/2011 | Mitsuno et al. |
| 2012/0041388 A1 | 2/2012 | Blomquist |
| 2012/0109072 A1 | 5/2012 | Tabata et al. |
| 2012/0220948 A1 | 8/2012 | Barbour |
| 2012/0279996 A1 | 11/2012 | Pappalardo et al. |
| 2013/0043282 A1 | 2/2013 | Niklasson |
| 2013/0053788 A1 | 2/2013 | Dugand et al. |
| 2013/0303993 A1 | 11/2013 | Evans et al. |
| 2014/0012227 A1 | 1/2014 | Sigg et al. |
| 2016/0144122 A1 | 5/2016 | Locati et al. |

FOREIGN PATENT DOCUMENTS

| | | |
|---|---|---|
| CA | 2312169 C | 9/2005 |
| DE | 19613035 A1 | 9/1997 |
| DE | 102004036051 A1 | 2/2006 |
| DE | 102005005468 A1 | 8/2006 |
| DE | 102006005784 A1 | 8/2006 |
| DE | 202012011016 U1 | 11/2012 |
| DE | 202013000688 U1 | 3/2013 |
| EP | 0649318 A1 | 4/1995 |
| EP | 0792659 A2 | 9/1997 |
| EP | 0871506 A2 | 10/1998 |
| EP | 1358899 A2 | 11/2003 |
| EP | 1566194 A2 | 8/2005 |
| EP | 2783720 A1 | 10/2014 |
| FR | 2830199 A1 | 4/2003 |
| JP | H11178923 A | 7/1999 |
| JP | 4044780 B2 | 2/2008 |
| JP | 4400112 B2 | 1/2010 |
| JP | 4447243 B2 | 4/2010 |
| JP | 5346231 B2 | 11/2013 |
| JP | 5518844 B2 | 6/2014 |
| JP | 5571767 B2 | 8/2014 |
| RU | 2423152 C2 | 7/2011 |
| WO | 2005089840 A1 | 9/2005 |
| WO | 2011023738 A1 | 3/2011 |
| WO | 2011122351 A1 | 10/2011 |
| WO | 2012041946 A1 | 4/2012 |
| WO | 2013009387 A1 | 1/2013 |
| WO | 2014025564 A1 | 2/2014 |
| WO | WO 2014025564 A1 * | 2/2014 ............ A61M 5/178 |
| WO | 2014033873 A1 | 3/2014 |

* cited by examiner

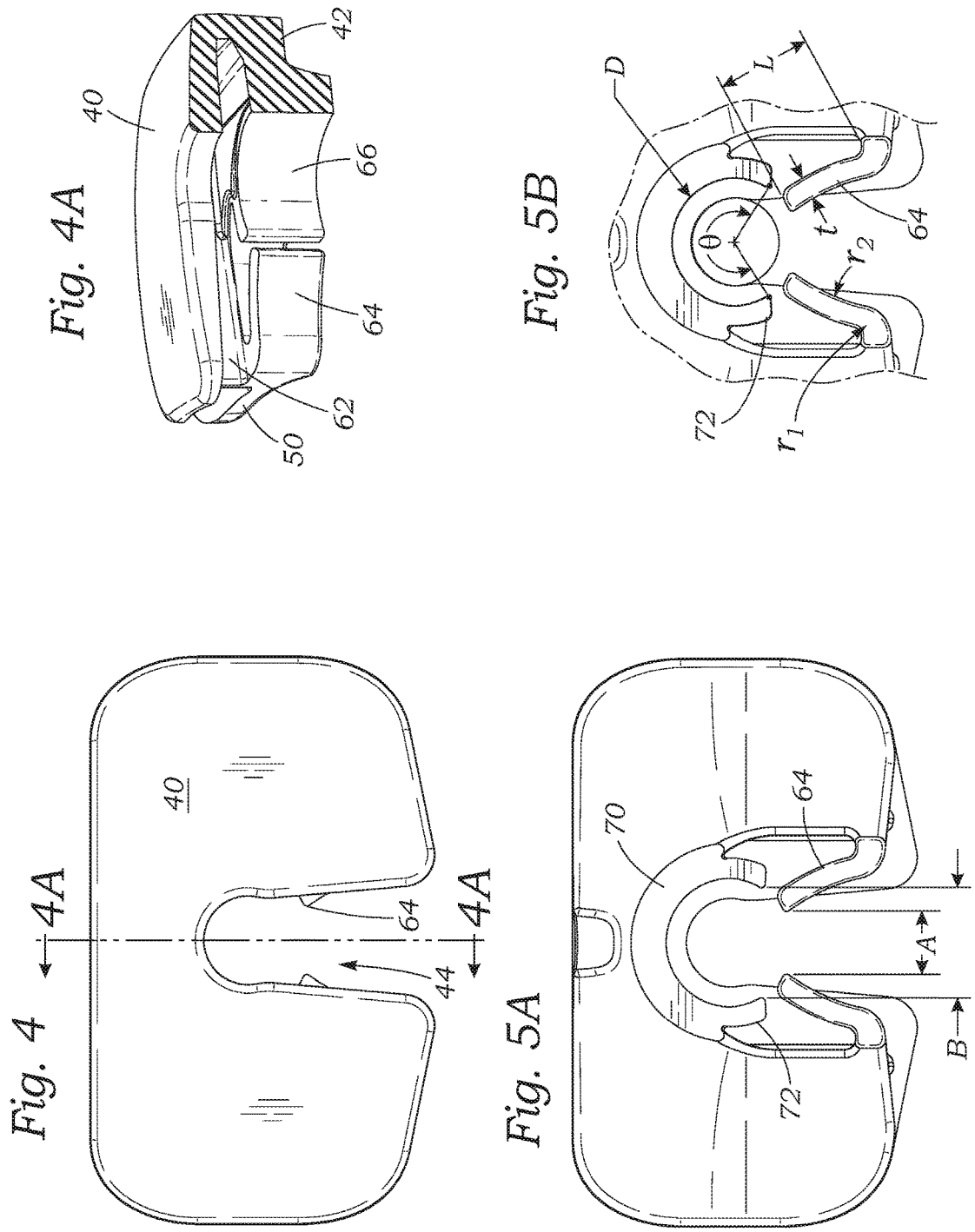

SYRINGE FINGER GRIP

FIELD OF THE INVENTION

The present invention relates to an adapter for a syringe and, more particularly, to a press-on finger grip especially useful for glass syringes pre-filled with a lubricating agent for ophthalmic surgery.

BACKGROUND OF THE INVENTION

During cataract surgery, the cataract is removed and an intraocular lens (IOL) may be implanted in the eye of a subject to replace the natural crystalline lens. The natural lens must first be removed, for instance, using a phacoemulsification system. The IOL is then generally implanted using an insertion apparatus or device that rolls, folds, or otherwise configures the lens for delivery through a small incision in the eye in a way that reduces trauma and expedites post-surgery healing.

The IOL is stored separately and transferred to an injector or cartridge just prior to delivery. Typically, the injector or cartridge is first partially filled with a liquid or gel, for example, a viscoelastic lubricating agent or "Ophthalmic Viscosurgical Device" (OVD). The lubricating agent facilitates passage of the IOL through the injector. The surgeon also injects some of the lubricating agent directly into the eye to facilitate insertion and positioning of the IOL. One family of viscoelastic substances used is sodium hyaluronate sold under the trade name Healon®, though Balanced Salt Solutions (BSS) and other lubricating agents are used.

Viscoelastic lubricating agents are commonly sold pre-filled in a syringe provided with a thin cannula tip. Glass syringes are used to avoid any degradation of the syringe and lubricating agent during storage. A syringe is typically gripped by the thumb and fingers in one hand and is used by depressing the plunger rod with the thumb axially along the syringe axis with the fingers holding a flange at the rear end of the syringe barrel. Due to manufacturing constraints with glass syringes, the flange at the rear end of the syringe barrel is relatively small and annular. Because of the thin cannula tip and viscoelastic nature of the lubricating agent, a relatively large squeezing force may be required and the small annular flange presents an ergonomic hindrance. Consequently, press-on finger grips are typically provided with the pre-filled syringe which snap onto the annular flange and greatly increase the surface area available.

U.S. Pat. No. 5,700,247 to Becton Dickinson France S.A. discloses a backstop device for a so-called flangeless syringe (which nonetheless has a small flange), which serves to provide a large finger grip. The backstop device has an opening that describes a partial circle which can be snapped over the cylindrical syringe barrel flange. Currently, Becton Dickinson markets a glass HYPAK syringe that is sold with a similar backstop device. Although the backstop device for the HYPAK syringe improves functionality by providing a large finger grip, it is only retained on the syringe by friction in a snap-fit arrangement, much like several other commercial finger grips. If a user places a rotational or horizontal force on the plunger relative to the finger grip, these devices can suddenly become disconnected from the syringe body. This can be extremely dangerous if the user is in the process of injecting lubricant into the eye.

It would be advantageous to provide a finger grip for syringes which avoids these disadvantages.

SUMMARY OF THE INVENTION

The present application relates to a finger grip for receiving and retaining a syringe body of an injection syringe. The device employs a centering feature and a pair of one way, flexible latches that allow easy attachment to a syringe body yet ensures retention during normal and abnormal use. The configuration of the finger grip ensures that if a high horizontal component force is applied during normal or abnormal use, the finger grip will not become disconnected in an uncontrolled fashion from the syringe body, which might cause injury and/or damage to a patient being injected.

BRIEF DESCRIPTION OF THE DRAWINGS

Embodiments of the present invention will be better understood from the following detailed description when read in conjunction with the accompanying drawings. Such embodiments, which are for illustrative purposes only, depict the novel and non-obvious aspects of the invention. The drawings include the following figures, with like numerals generally indicating like parts:

FIG. 4 is a top plan view of the exemplary finger grip showing an entrance slot and inner ends of a pair of resilient locking latches, and FIG. 4A is a vertical sectional view through the entrance slot taken along line 4A-4A of FIG. 4;

FIG. 5A is a bottom plan view of the exemplary finger grip showing width dimensions of an entrance slot, and FIG. 5B is an isolation of the entrance slot with several other exemplary dimensions;

DETAILED DESCRIPTION OF THE PREFERRED EMBODIMENTS

The present invention facilitates the use of syringes which have relatively small finger flanges requiring an adapter to enlarge the finger grip. The adapter presses or snaps onto the existing finger flange to provide a large surface area finger grip and provide a more ergonomic injection action. The finger grip includes a pair of resilient locking latches which prevent detachment of the finger grip from the syringe even in the case of large offset compressive forces. Preferably, the locking latches prevent detachment of the finger grip from the syringe up to and including the point where the plunger rod breaks or deforms. Even if the finger grip were pulled perpendicularly away from the syringe, the user would need to break the locking latches to detach the finger grip.

The finger grip described herein is particularly useful to enhance the operation of a syringe pre-filled with a viscoelastic lubricating agent during ophthalmic surgery. The syringes are made of glass and thus have a relatively small finger flange requiring an add-on finger grip. Furthermore, the locking nature of the exemplary finger grip prevents the sudden detachment from the syringe at a moment when the thin cannula tip may be inserted in the eye. However, the add-on finger grip may also be useful for other syringe applications, and it should be understood that the scope of the present application is only limited by the appended claims. For example, although the finger grips described herein are especially useful to adapt glass syringes, they may also be connected to plastic syringes to the same effect.

Figure 1:
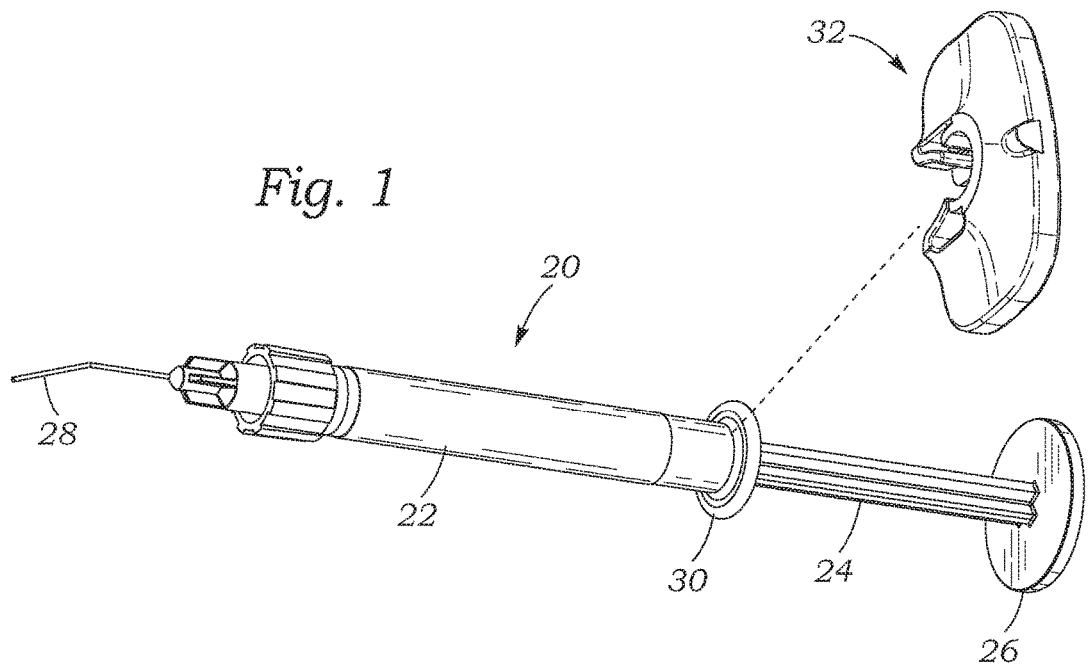
FIG. 1 is a perspective view of an exemplary pre-filled syringe having a small finger flange and showing a press-on finger grip of the present application exploded therefrom.

FIG. 1 is a perspective view of an exemplary pre-filled syringe 20 having a cylindrical barrel 22 with an inner cavity for containing a volume of medium to be ejected. A plunger including a plunger rod 24 and thumb plate 26 may be depressed to expel the medium from within the barrel 22. In the illustrated embodiment, the syringe 20 is intended for use in ophthalmic surgery and has a relatively thin distal cannula tip 28 through which a viscoelastic medium or lubricating agent may be expelled. The thin cannula tip 28 may be advanced directly into the eye for injecting the lubricating agent held in the barrel 22.

Figure 2:
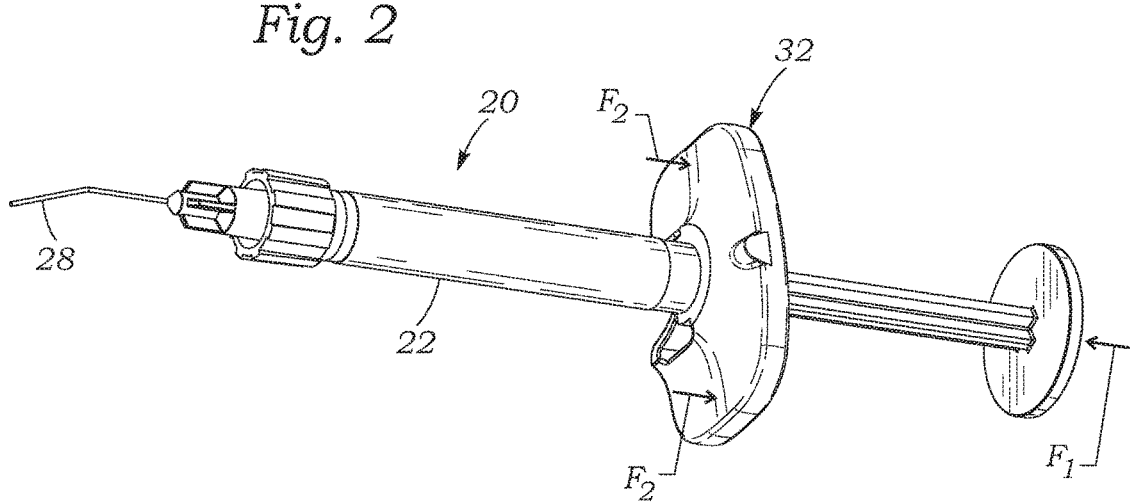
FIG. 2 is a perspective view as in FIG. 1 showing the finger grip assembled over the finger flange on the syringe.

A small annular finger flange 30 circumscribes a proximal end of the syringe barrel 22. As explained, the syringe barrels 22 used for holding viscoelastic lubricating agents are made of inert glass to prevent any chemical reactions or leaching, which might occur with plastic syringes, and as such the finger flange 30 is relatively small in diameter because of glass manufacturing constraints. This would be relatively uncomfortable for the user, and thus FIG. 1 shows a press-on finger grip 32 of the present application exploded therefrom. FIG. 2 shows the finger grip 32 assembled over the finger flange 30 on the syringe 20. As will be explained below, the finger grip 32 includes a locking feature which allows it to be laterally pressed onto the finger flange 30 and remain in place even in the case of an inordinate amount of off-axis compressive forces applied to the syringe.

FIGS. 3A-3D are several perspective views of the exemplary finger grip 32, which has a thin, generally rectangular body with an upper face 40, and a lower face 42 separated into two longitudinal sides (see FIG. 3B) by a syringe-receiving slot 44 that receives the barrel 22 of the syringe 20. A vertical axis 46 through the inner or closed end of the syringe-receiving slot 44 defines upper and lower directions, and defines horizontal planes that are perpendicular therethrough. The finger grip 32 features a front edge 50 bifurcated by the syringe-receiving slot 44, a continuous rear edge 52, and two shorter laterally-extending side edges 54. The finger grip 32 is termed generally rectangular because the front and rear edges 50, 52 extend longitudinally generally in parallel and are longer than the side edges 54, also generally in parallel. However, all of the edges 50, 52, 54 have rounded corners at their intersections and at the intersections with the top and bottom faces 40, 42, and the rear edge 52 is slightly concave. Furthermore, the upper face 40 has a convex curvature, while the lower face 42 is slightly concave on both longitudinal sides of the syringe-receiving slot 44. It should be understood that the overall shape of the finger grip 32 may be more or less angular or circulate/oval in shape, as long as there remain two wings extending on either side of the slot 44 that form finger rests or braces. When coupled to the syringe 20, as seen in FIG. 2, the user may actuate the syringe by placing two fingers under the concave sides of the lower face 42 with a thumb pressing on the thumb plate 26 to depress the plunger. The axial compressive forces that are applied to expel the medium from the syringe barrel 22 are shown by the large force arrows: $F_1$ for the thumb and $F_2$ for the fingers.

The entire finger grip 32 is desirably molded as a single piece from a suitable polymer such as polypropylene, and a number of cavities are formed therein to reduce the overall weight of the finger grip. Namely, as seen from the front in FIG. 3C, the upper face 40 is spaced from the lower face 42 by a pair of generally triangular cavities 60 that extend therebetween. In addition to the syringe-receiving slot 44, the finger grip 32 defines a horizontal slot 62 that extends generally coextensive with the entrance slot but is both wider and deeper. The horizontal slot 62 receives the flange 30 of the syringe 20 when the finger grip 32 and syringe are coupled together. In a preferred embodiment, the finger grip 32 is fabricated using a sliding mold to form the various shapes. For instance, core or mold inserts are used to form the generally horizontal walls defining the cavities 60 and horizontal slot 62, which mold inserts are then retracted in a frontal direction when the workpiece is sufficiently cooled.

Figure 3B:
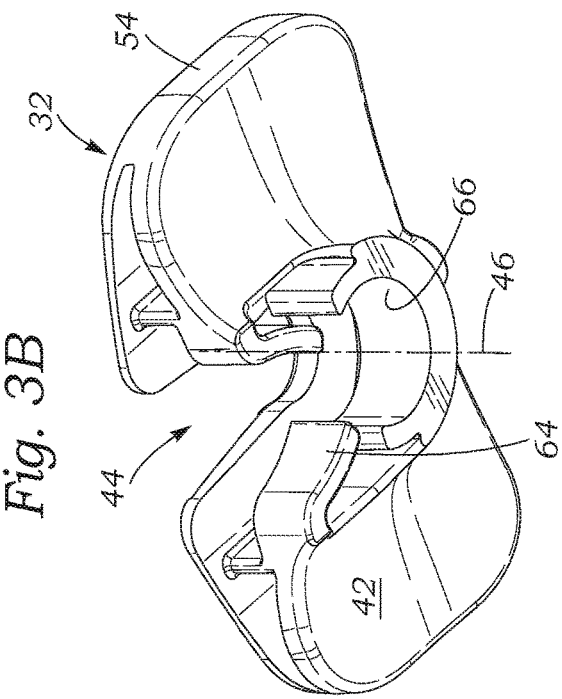
FIGS. 3A-3D are different perspective views of the exemplary finger grip.
Figure 3D:
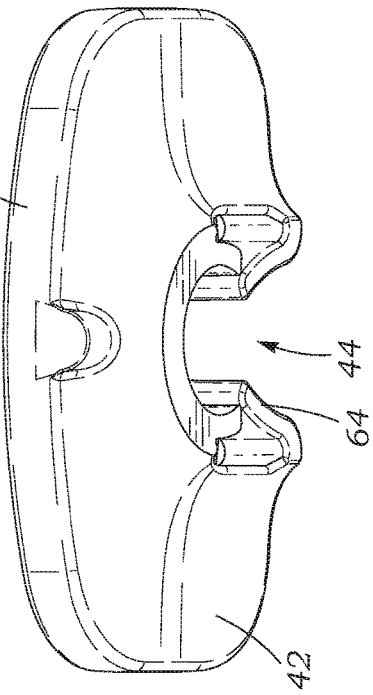
Figure 3A:
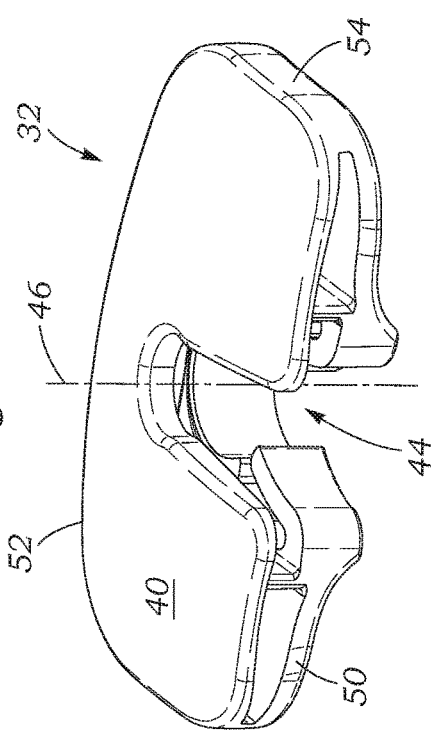
Figure 3C:
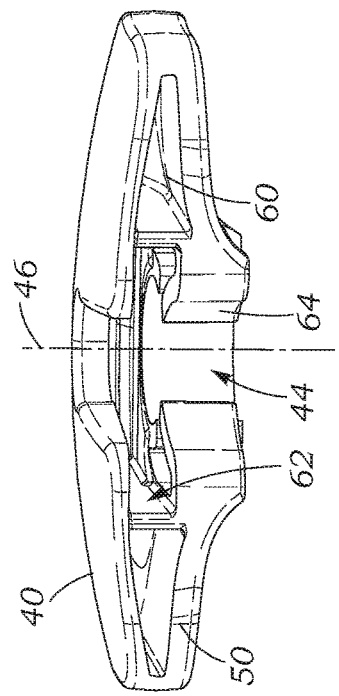

With reference to FIGS. 3B and 3C, the syringe-receiving slot 44 is defined partly by inner edges of a slot formed in the upper face 40 as well as by structures contiguous with the lower face 42 that border the entrance slot. In particular, the lower portion of the syringe-receiving slot 44 includes opposite inner edges from which a pair of curved latches 64 extend and a partial tubular receptacle 66. Both the latches 64 and receptacle 66 are defined by vertically-oriented walls that project downward below the lower face 42. The curved latches 64 project from the front edge 50 rearward and inward toward each other into the syringe-receiving slot 44. The receptacle 66 is located rear of a longitudinal midplane of the finger grip 32 and defines a terminus or dead end of the syringe-receiving slot 44. It will be understood that the sliding mold preferably used to form the finger grip 32 has core or mold inserts that form the generally vertical walls defining the slot 44 and latches 64 that retract in a vertical direction from the workpiece once it is formed and sufficiently cooled.

FIG. 4 is a top plan view of the exemplary finger grip 32 and FIG. 4A is a vertical sectional view through the syringe-receiving slot 44 taken along line 4A-4A of FIG. 4. Just the inner tips of the curved latches 64 are visible in the syringe-receiving slot 44 looking from above in FIG. 4. The vertical dimensions of both the curved latches 64 and receptacle 66 relative to the upper face 40 and lower face 42 are shown clearly in FIG. 4, which also shows the width and depth of the horizontal flange-receiving slot 62 relative to the syringe-receiving slot 44.

FIGS. 5A and 5B are bottom plan views of the finger grip 32 showing various dimensions of the syringe-receiving slot 44. First of all, the inner tips of the curved latches 64 are spaced apart a dimension A. Each of the latches 64 initially curves to the rear from the front wall 50 about a radius $r_1$, and then reaches an inflection point after which both latches curve toward each other about a radius $r_2$. That is, the latches 64 are multicurvate with an inflection point. Latches 64 have a thickness t and a length L. The receptacle 66 includes a relatively thick semicircular portion 70 having an inner diameter D continuing forward into two somewhat thinner short cantilevered tails 72 that define the same inner curvature. The inner tips of the tails 72 are spaced apart a dimension B, and the entire inner wall of the receptacle 66 extends around an angle θ.

These dimensions will differ depending on the size of the syringe barrel 22 being gripped. However, it will be understood that B>A, or in other words the tails 72 are spaced farther apart than the inner tips of the latches 64. The dimension B corresponds to the chordal length on the circle having the diameter D drawn between the inner tips of the tails 72. This chordal length also depends on the included angle θ around the inner wall of the receptacle 66. A more complete discussion of the preferred dimensions will be provided below following a description of how the finger grip 32 holds the syringe 20.

Figure 6A:
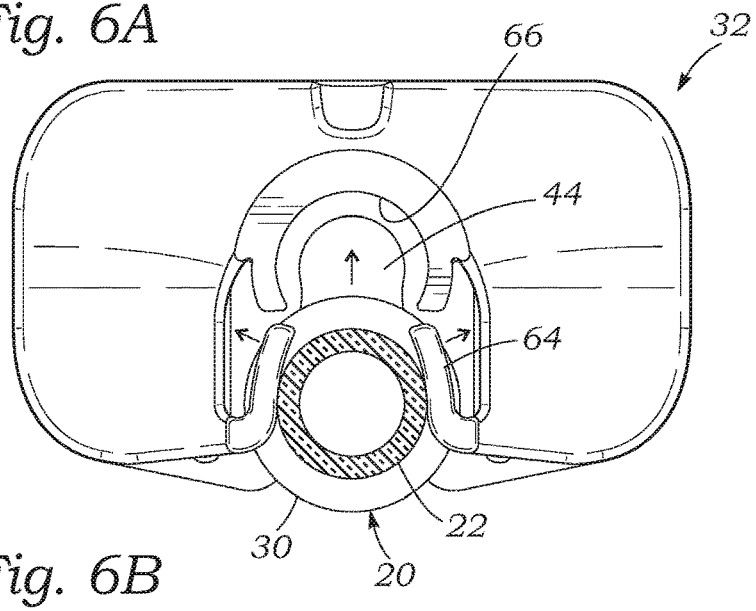
FIGS. 6A-6C are bottom plan views of the finger grip showing insertion of a syringe barrel past the locking latches so as to be secured in a receiving receptacle.
Figure 6B:
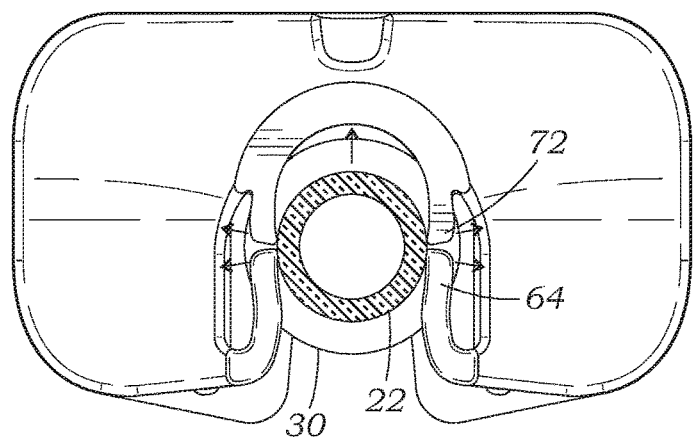
Figure 6C:
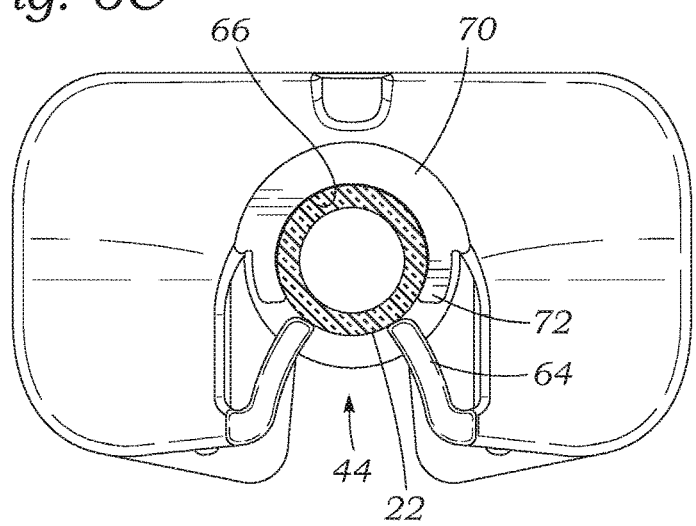

FIGS. 6A-6C are bottom plan views of the finger grip 32 showing insertion of a syringe barrel 22 into the syringe-receiving slot 44 past the one-way locking latches 64 so as to be secured in the receiving receptacle 66. Initially, as in FIG. 6A, the user inserts the syringe 20 into the beginning of the syringe-receiving slot 44 until the syringe barrel 22 contacts both of the locking latches 64 and begins to flex them outward, as indicated. The syringe flange 30 fits closely within the flange-receiving slot 62 (FIG. 3C). The outermost bends of the latches 64, having a radius $r_1$ as seen in FIG. 5B, present nicely rounded corners that funnel the tubular syringe barrel 22 into the receptacle 44 and facilitate the gradual outward flexing of the latches.

FIG. 6B shows the syringe barrel 22 about halfway into the syringe-receiving slot 44 at a point where the latches 64 are at their maximum outward deflection. The cantilevered latches 64 are dimensioned and flexible enough such that the inward reaction force on the syringe barrel 22 is not so great as to potentially break the glass barrel. The syringe barrel 22 has a diameter that is greater than the dimension B between the cantilevered tails 72, and thus the tails are also flexed outward as indicated. The tails 72 are spaced apart a distance large enough that they do not prevent insertion of the syringe barrel 22 into the receptacle 66, but less than the syringe barrel diameter so that they flex outward and provide some holding force once the syringe is seated within the receptacle 66. Furthermore, the tails 72 accommodate insertion of a range of diameters of syringe.

Finally, FIG. 6C shows the syringe barrel 22 fully seated within the receptacle 66. In this illustration, the outer diameter of the syringe barrel 22 closely matches the diameter D of the receiving receptacle 66 such that the cantilevered tails 72 spring back toward each other into a relaxed, unstressed condition. Because the tails 72 are spaced apart a distance B less than the outer diameter of the syringe barrel, they serve to frictionally hold the syringe in place. However, if the tails 72 were the only retaining force the syringe 20 could still pop out of the finger grip 32 if improper misaligned forces were applied to the syringe plunger, for example.

The present finger grip 32 further includes the one-way locking latches 64 which spring back toward each other into the relaxed, unstressed positions shown. The tips of the latches 64 abut or are closely adjacent to the exterior of the syringe barrel 22, and provide a positive retention barrier to the syringe exiting the syringe-receiving slot 44. Thus, the latches 64 enable a one-way introduction of the syringe into the receptacle 66 but prevent removal. The dimensions of the latches 64 and their spacing A ensure that they cannot be flexed apart by a reverse movement of the syringe barrel 22. That is, if an attempt were made to pull the syringe barrel 22 out of the slot 44, the latches 64 would primarily be placed in compression, and the small torsional forces on them would tend to flex them closer together, as opposed to farther apart. In other words, even if excessive force was applied to pull the syringe from within the slot 44, the latches 64 would eventually break rather than be flexed apart. In this sense, the latches 64 function something like a tire spike at the exit of the parking lot which can be pushed downward below the pavement level when cars roll out, but remain upright when a car rolls over them in the opposite direction. In a preferred embodiment, the latches 64 have a holding force of at least 25 lbs, which is far greater than any potential misalignment forces applied by a user's hand. This contrasts with an average force of about 7 lbs necessary to detach currently sold commercial finger grips from syringes. It has been deduced from empirical tests that a misalignment force of about 25 lbs can be generated depending on the style of grip, which means the latches are strong enough to prevent removal of the syringe barrel from the syringe-receiving slot 44 up to at least a threshold lateral detachment force of about 25 lbs.

With reference back to FIGS. 5A and 5B, the dimensions illustrated may be quantified using an example where the diameter of the syringe barrel 22 is between 0.30-0.32 inches (7.62-8.13 mm), with a specific example of 0.317 inches (8.05 mm). The diameter D of the receiving receptacle 66 will preferably equal the syringe diameter, such that D=0.317±0.002 inches (8.05±0.05 mm). The included angle θ is between about 100-130°, and more preferably 115°. Consequently, a chord drawn between the inner tips of the tails 72 (dimension B) is between about 0.243-0.312 inches, and more preferably is about 0.287 inches (7.3 mm). The inner tips of the latches 64 are spaced apart (dimension A) by about 0.168 inches (4.27 mm). The latches preferably have a length L of about 0.232 inches (5.9 mm), and a thickness t about 0.055 inches (1.4 mm). The radius $r_1$ is about 0.073 inches (1.8 mm), and the radius $r_2$ is about 0.449 inches (11.4 mm). Of course, these dimensions are exemplary only and may be modified for smaller or larger syringes, and to obtain a greater or larger holding force of the locking latches 64.

Figure 7A:
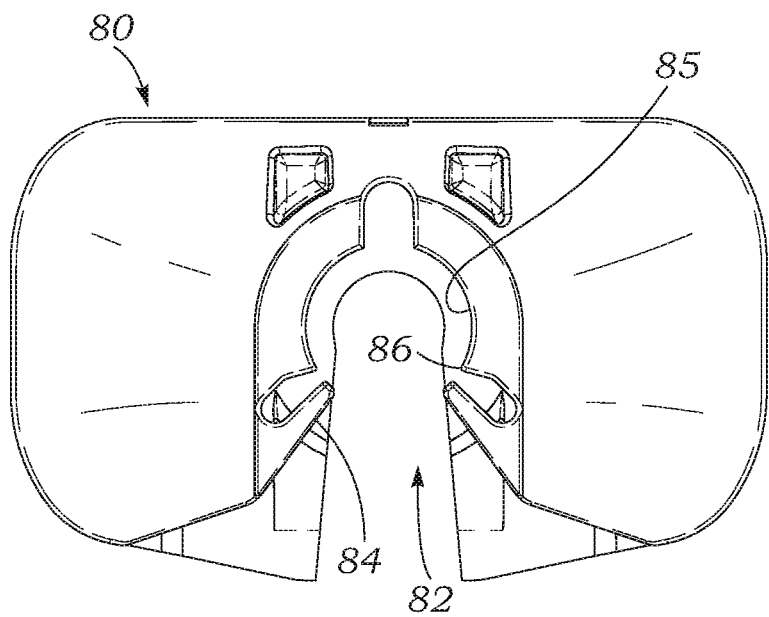
FIGS. 7A and 7B are bottom plan views of alternative finger grip configurations.
Figure 7B:
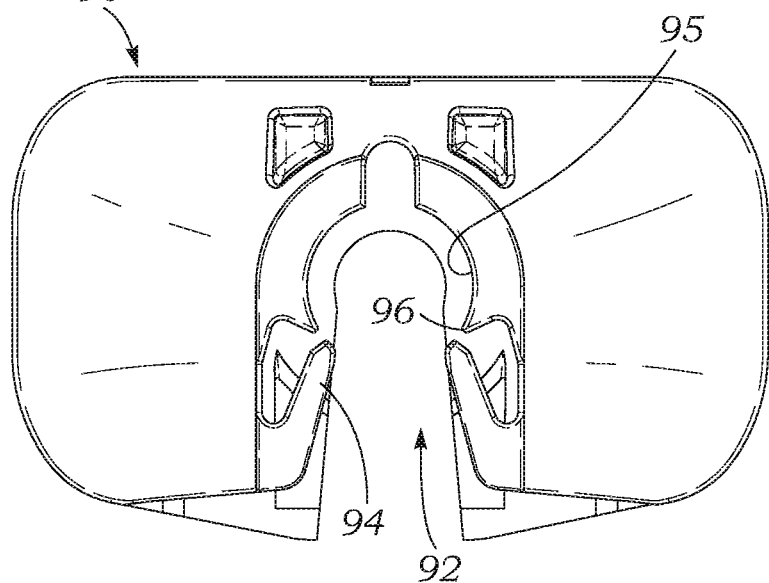

FIGS. 7A and 7B are bottom plan views of alternative finger grip configurations. FIG. 7A shows a finger grip 80 having a syringe-receiving slot 82 commencing with a pair of locking latches 84. The latches 84 extend in substantially the same orientation as the latches 64 described above, but are not formed with multiple curvatures. Instead, the latches 84 are generally triangular in plan view extending straight back at an angle toward the dead-end receiving receptacle 85 of the slot 82. Furthermore, rather than employing cantilevered tails at the mouth of the receptacle 85 as above, the material defining the receiving receptacle 85 tapers down to a pair of sharp corners 86 define the beginning of the receptacle. These corners 86 are desirably spaced apart a distance less than the diameter of the syringe being held, and thus flex apart upon entry of the syringe and hold the syringe in place.

FIG. 7B shows a finger grip 90 having a syringe-receiving slot 92 commencing with a pair of locking latches 94. The latches 94 extend in substantially the same orientation as the latches 80, and are generally triangular in plan view extending straight back at an angle toward the receiving receptacle 95 of the slot 92. Cantilevered tails 96 at the mouth of the receptacle 95 are desirably spaced apart a distance less than the diameter of the syringe being held, and thus flex apart upon entry of the syringe and hold the syringe in place. Both the latches 94 and the tails 96 narrow to points rather than having rounded ends, but otherwise they function similar to the latches and tails described above with respect to the first embodiment.

The above presents a description of the best mode contemplated of carrying out the present invention, and of the manner and process of making and using it, in such full, clear, concise, and exact terms as to enable any person skilled in the art to which it pertains to make and use this invention. This invention is, however, susceptible to modifications and alternate constructions from that described above which are fully equivalent. Consequently, it is not the intention to limit this invention to the particular embodiments disclosed. On the contrary, the intention is to cover modifications and alternate constructions coming within the spirit and scope of the invention as generally expressed by the following claims, which particularly point out and distinctly claim the subject matter of the invention.

What is claimed is:

1. A single-piece molded finger grip adapted to be coupled to a syringe having a barrel with a barrel diameter and a rear finger flange, comprising:
a single-piece molded body having an upper face and a lower face and a syringe-receiving slot that opens to a first longitudinal side edge of the body, the syringe-receiving slot having first and second longitudinal sides, wherein the body defines two finger rests each of which are on the respective first and second longitudinal sides of the syringe-receiving slot, the body defining a pair of cantilevered locking latches that project from opposite inside edges of the syringe-receiving slot toward each other and have inner tips that are spaced apart a distance less than the barrel diameter, the locking latches being angled from the opposite inside edges of the syringe-receiving slot toward each other and toward a dead-end receptacle of the syringe-receiving slot, the dead-end receptacle having an inner diameter that is approximately the same as the barrel diameter, and the locking latches are configured to have sufficient flexibility such that the barrel is inserted into the syringe-receiving slot by flexing the locking latches apart, the locking latches are configured to have a length such that when the barrel is seated within the dead-end receptacle, the locking latches spring back to a relaxed configuration, wherein any force on the barrel in a direction out of the dead-end receptacle would tend to flex the locking latches closer together and prevent removal of the barrel from the syringe-receiving slot.

2. The finger grip of claim 1, wherein the locking latches prevent removal of the barrel from the syringe-receiving slot up to at least a threshold lateral detachment force of about 25 lbs.

3. The finger grip of claim 1, wherein the finger grip further includes a flange-receiving slot that opens to the first longitudinal side edge of the body sized to receive the finger flange of the syringe, the flange-receiving slot being adjacent to and larger than the syringe-receiving slot.

4. The finger grip of claim 1, wherein the upper face is convex, and the lower face on the first longitudinal side and the lower face on the second longitudinal side of the syringe-receiving slot are concave.

5. The finger grip of claim 1, wherein the dead-end receptacle has an inner circular wall that defines an included angle of between 100°-130°.

6. The finger grip of claim 5, wherein the dead-end receptacle terminates at an open mouth at a pair of flexible tails.

7. The finger grip of claim 6, wherein the flexible tails are cantilevered and spaced apart a distance less than the barrel diameter so that they flex outward when the barrel is seated within the dead-end receptacle.

8. A single-piece molded finger grip adapted to be coupled to a syringe having a barrel with a barrel diameter and a rear finger flange, comprising:
a single-piece molded body defining a horizontal plane and having upper and lower faces spaced apart along a vertical axis, the body defining two pairs of opposed side edges between the upper and lower faces and being proportionally thinner in the vertical axis than in the horizontal plane;
a syringe-receiving slot in the body that bifurcates one side edge of the two pairs of the opposed side edges and ends at a dead-end receptacle having an inner diameter that is approximately the same as the barrel diameter, wherein the body has first and second longitudinal sides and defines two finger rests on the respective first and second longitudinal sides of the syringe-receiving slot;
a pair of cantilevered locking latches that project from opposite inside edges of the syringe-receiving slot toward each other and have inner tips that are spaced apart a distance less than the barrel diameter, the locking latches are configured to have sufficient flexibility such that the barrel is inserted into the syringe-receiving slot by flexing the locking latches apart, wherein the locking latches are configured to spring back to a relaxed configuration upon passage of the barrel and are shaped and oriented to prevent removal of the barrel from the syringe-receiving slot straight out from between the locking latches short of a force that breaks the locking latches and in the absence of any force on the locking latches other than from the syringe.

9. The finger grip of claim 8, wherein the locking latches prevent removal of the barrel from the syringe-receiving slot up to at least a threshold lateral detachment force of about 25 lbs.

10. The finger grip of claim 8, wherein the dead-end receptacle has an inner circular wall that defines an included angle of between 100°-130°.

11. The finger grip of claim 10, wherein the dead-end receptacle terminates at an open mouth at a pair of flexible tails.

12. The finger grip of claim 11, wherein the flexible tails are cantilevered and spaced apart a distance less than the barrel diameter so that they flex outward when the barrel is seated within the dead-end receptacle.

13. The finger grip of claim 8, wherein the dead-end receptacle and the locking latches are formed by vertical walls in the molded body, while the flange-receiving slot is formed by generally horizontal walls in the molded body.

14. The finger grip of claim 8, wherein the locking latches are angled from the opposite inside edges of the syringe-receiving slot toward each other and toward the dead-end receptacle, and are multicurvate with an inflection point.

* * * * *